United States Patent
Lee et al.

(10) Patent No.: US 11,759,183 B2
(45) Date of Patent: Sep. 19, 2023

(54) ULTRASOUND PROBE, ULTRASOUND IMAGING APPARATUS AND CONTROL METHOD THEREOF

(71) Applicant: SAMSUNG MEDISON CO., LTD., Gangwon-do (KR)

(72) Inventors: Sungjae Lee, Seoul (KR); Sangmok Lee, Seoul (KR); Yongcheol Hyeon, Seoul (KR)

(73) Assignee: SAMSUNG MEDISON CO. LTD., Gangwon-Do (KR)

(*) Notice: Subject to any disclaimer, the term of this patent is extended or adjusted under 35 U.S.C. 154(b) by 0 days.

(21) Appl. No.: 17/190,929

(22) Filed: Mar. 3, 2021

(65) Prior Publication Data
US 2021/0298723 A1    Sep. 30, 2021

(30) Foreign Application Priority Data

Mar. 24, 2020 (KR) .................. 10-2020-0035732

(51) Int. Cl.
*A61B 8/00* (2006.01)
*A61B 8/12* (2006.01)
*A61B 8/14* (2006.01)

(52) U.S. Cl.
CPC .................. *A61B 8/54* (2013.01); *A61B 8/12* (2013.01); *A61B 8/463* (2013.01); *A61B 8/56* (2013.01); *A61B 8/58* (2013.01); *A61B 8/14* (2013.01)

(58) Field of Classification Search
CPC .. A61B 8/54; A61B 8/12; A61B 8/463; A61B 8/56; A61B 8/58; A61B 8/14;
(Continued)

(56) References Cited

U.S. PATENT DOCUMENTS 5,517,994 A * 5/1996 Burke .................. G01S 7/5205
600/443
6,542,846 B1 * 4/2003 Miller ................. G01S 7/52096
702/132

(Continued)

FOREIGN PATENT DOCUMENTS

EP          3 1757 93 A1     6/2017
JP          2017-079048 A    4/2017
KR       10-1999-0028651 A   4/1999

OTHER PUBLICATIONS

Extended European Search Report dated Aug. 20, 2021, issued in corresponding European Patent Application No. 21161537.2.

(Continued)

*Primary Examiner* — Pascal M Bui Pho
*Assistant Examiner* — Michael Yiming Fang
(74) *Attorney, Agent, or Firm* — Morgan, Lewis & Bockius LLP

(57) ABSTRACT

The present disclosure provides an ultrasound probe, an ultrasound imaging apparatus, and a control method thereof that can efficiently and quickly determine whether a disinfectant remains in an ultrasound probe or whether the ultrasound is operating normally without changing the structure of an ultrasound imaging device. The ultrasound imaging apparatus of an embodiment includes: a display provided on the main body; a main body including at least one slot connected to the connector; and a controller configured to output a warning message to the display when the connector and the slot are connected and the current flowing from the ultrasound probe is out of a predetermined reference range, and the controller is composed of at least one processor included in the main body.

10 Claims, 11 Drawing Sheets

(58) Field of Classification Search
CPC ....... A61B 8/4405; A61B 8/4422; A61B 8/44; A61B 8/466; A61B 8/46; A61B 2560/0266; G01S 7/5205; G01S 7/52053; G01S 15/8915
See application file for complete search history.

(56) References Cited

U.S. PATENT DOCUMENTS

| | | | |
|---|---|---|---|
| 6,772,380 B1 * | 8/2004 | Ali | G01R 31/69 714/724 |
| 8,382,666 B1 * | 2/2013 | Mao | G02B 6/4219 600/202 |
| 9,157,880 B2 | 10/2015 | Stevens et al. | |
| 9,490,625 B2 | 11/2016 | Tanimoto et al. | |
| 10,026,572 B2 | 7/2018 | Shimura et al. | |
| 2012/0215213 A1 * | 8/2012 | Juzkiw | A61B 18/14 606/34 |
| 2014/0171802 A1 * | 6/2014 | Kuroiwa | A61B 8/4477 600/459 |
| 2014/0184383 A1 * | 7/2014 | Wodnicki | A61B 8/4483 340/4.3 |
| 2014/0276055 A1 * | 9/2014 | Barthe | A61B 8/4466 600/439 |
| 2015/0157299 A1 * | 6/2015 | Hopple | B06B 1/0207 600/459 |
| 2015/0327839 A1 * | 11/2015 | Kim | A61B 8/56 600/447 |
| 2017/0160329 A1 * | 6/2017 | Jeon | G01S 7/5205 |
| 2018/0356493 A1 * | 12/2018 | Stapert | A61B 8/12 |
| 2020/0300817 A1 * | 9/2020 | Yazaki | G01N 29/34 |

OTHER PUBLICATIONS

European Communication dated Mar. 6, 2023 issued in European Patent Application No. 21161537.2.

* cited by examiner

ULTRASOUND PROBE, ULTRASOUND IMAGING APPARATUS AND CONTROL METHOD THEREOF

CROSS-REFERENCE TO RELATED APPLICATION

This application is based on and claims priority under 35 U.S.C. § 119 to Korean Patent Application No. 10-2020-0035732, filed on Mar. 24, 2020 in the Korean Intellectual Property Office, the disclosure of which is incorporated herein by reference.

BACKGROUND

1. Technical Field

The disclosure relates to an ultrasound probe, an ultrasound imaging apparatus, and a control method thereof for determining whether or not a disinfectant remains in the ultrasound probe.

2. Description of the Related Art

The probe of the ultrasound diagnosis device directly contacts the affected part of the subject to perform diagnosis/test.

The disinfection of the probe is essential because if there is a contaminant of the probe or a skin disease of the test subject, it may cause infection to another subject. The ultrasound probe is cleaned with a liquid disinfectant according to sterilization and disinfection. Accordingly, the ultrasound diagnosis device is also subject to inspection for sterilization/disinfectant, and after disinfection, the user performs a checkup for the subject.

Furthermore, high-level disinfection and sterilization is essential for ultrasound probes, and guidelines are constantly being made and supplemented accordingly. For disinfection of ultrasound probes, hospitals generally use simple and time-saving machine cleaning.

Recently, a lot of products with a structure to connect connector terminals have been widely used. If the ultrasound probe is put in a sterilizer in a hospital for cleaning, the disinfectant may penetrate and remain inside the connector of the ultrasound probe. In that case, when the user does not recognize it and uses it, overcurrent/overvoltage occurs due to short-circuiting of the ultrasound probe with the portable device, which may cause malfunction.

Also, the imaging performance of these ultrasound probes can be greatly degraded.

Therefore, in order to prevent this phenomenon, there is a need for a technology to determine whether or not disinfectants, etc. remain in the ultrasound probe.

SUMMARY

The present disclosure provides an ultrasound probe, an ultrasound imaging apparatus, and a control method thereof that can efficiently and quickly determine whether a disinfectant remains in an ultrasound probe or whether the ultrasound is operating normally without changing the structure of an ultrasound imaging device.

Therefore, it is an aspect of the disclosure to provide an ultrasound imaging apparatus including: a display provided on the main body; a main body including at least one slot connected to the connector; and a controller configured to output a warning message to the display when the connector and the slot are connected and the current flowing from the ultrasound probe is out of a predetermined reference range, and the controller is composed of at least one processor included in the main body.

The controller may be configured to output a warning message to the display when the identification current identifying the ultrasound probe is out of a predetermined reference range.

The controller may be configured to output a warning message to the display when the test current of the element of the ultrasound probe is out of a predetermined reference range.

The main body may include an overcurrent protection circuit, and the controller may be configured to output a warning message to the display when the current flowing from the ultrasound probe to the overcurrent protection circuit is out of a predetermined reference range.

The current flowing from the ultrasound probe may be used as a test signal for self-diagnosis of the ultrasound probe.

The controller may be configured to determine that a failure has occurred in the connector and output a warning message corresponding to the failure of the connector to the display when the current flowing from the ultrasound probe is included in a predetermined error range.

The ultrasound probe may be provided as an insertion type probe.

The ultrasound probe may include an own display, and the controller may be configured to output the warning message to the own display.

It is an aspect of the disclosure to provide a control method of an ultrasound imaging apparatus including an ultrasound probe including a connector, a display provided on the main body and a main body including at least one slot connected to the connector, the method includes: outputting a warning message to the display when the connector and the slot are connected and the current flowing from the ultrasound probe is out of a predetermined reference range.

The outputting a warning message may include: outputting a warning message to the display when the identification current identifying the ultrasound probe is out of a predetermined reference range.

The outputting a warning message may include: outputting a warning message to the display when the test current of the element of the ultrasound probe is out of a predetermined reference range.

The main body may include an overcurrent protection circuit, and the outputting a warning message may include: outputting a warning message to the display when the current flowing from the ultrasound probe to the overcurrent protection circuit is out of a predetermined reference range.

The current flowing from the ultrasound probe may be used as a test signal for self-diagnosis of the ultrasound probe.

The outputting a warning message may include: determining that a failure has occurred in the connector and outputting a warning message corresponding to the failure of the connector to the display when the current flowing from the ultrasound probe is includes in a predetermined error range.

The ultrasound probe may be provided as an insertion type probe.

The ultrasound probe may include an own display, and the outputting a warning message may include: outputting the warning message to the own display.

It is an aspect of the disclosure to provide an ultrasound probe including: a probe power supply; a connector connected to another device; an own display; and at least one processor configured to output a warning message to the own display when the current flowing through the connector by receiving power from the power supply is out of a predetermined reference range.

The probe power supply may be charged from the power supplied by another device when the connector is connected to the at least another device, and the ultrasound probe transmits and receives an ultrasound signal.

The at least one processor may be configured to control the probe power supply to supply current to the connector when a user inputs a self-diagnosis command.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
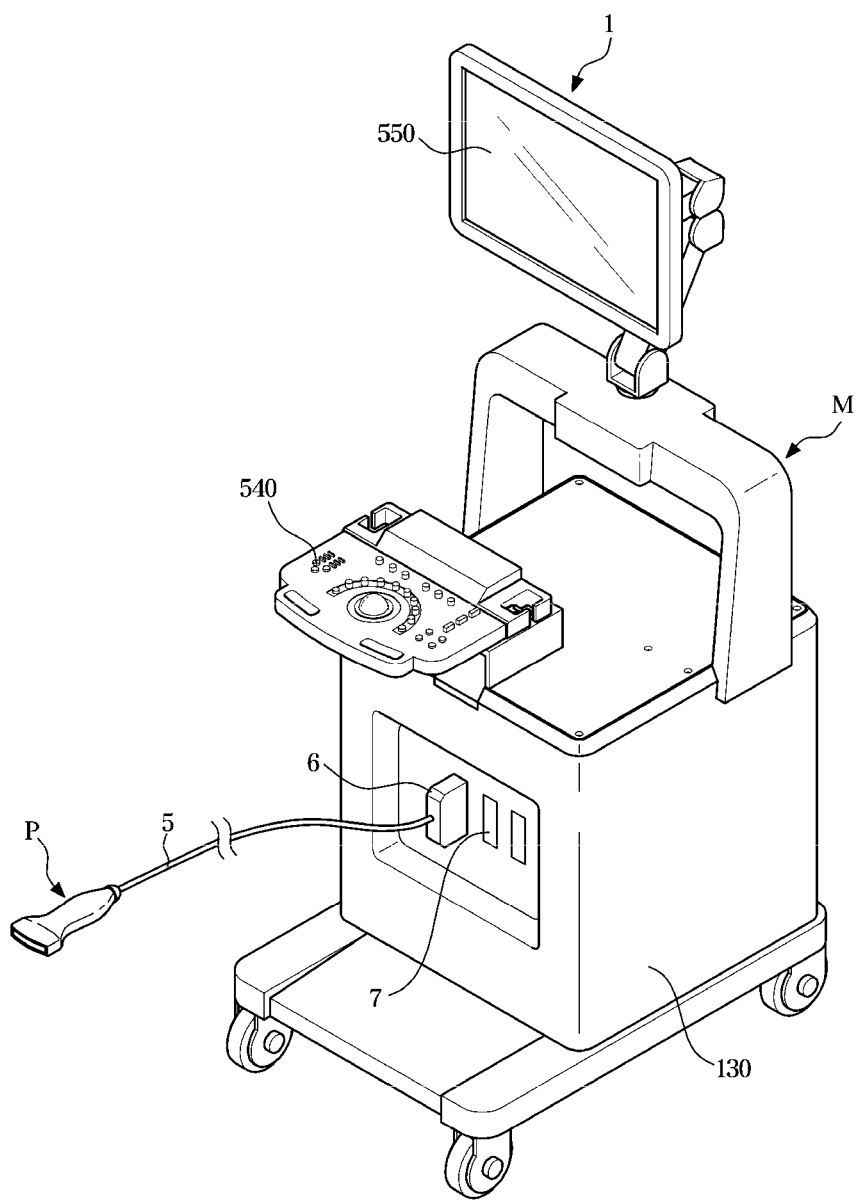
FIG. 1 is a view illustrating an appearance of an ultrasound imaging apparatus according to an embodiment of the disclosure.

Like reference numerals refer to like elements throughout the specification. Not all elements of embodiments of the disclosure will be described, and description of what are commonly known in the art or what overlap each other in the embodiments will be omitted. The terms as used throughout the specification, such as "~ part," "~ module," "~ member," "~ block," etc., may be implemented in software and/or hardware, and a plurality of "~ parts," "~ modules," "~ members," or "~ blocks" may be implemented in a single element, or a single "~ part," "~ module," "~ member," or "~ block" may include a plurality of elements.

It will be understood that when an element is referred to as being "connected" to another element, it can be directly or indirectly connected to the other element, wherein the indirect connection includes "connection" via a wireless communication network.

Also, when a part "includes" or "comprises" an element, unless there is a particular description contrary thereto, the part may further include other elements, not excluding the other elements.

Further, when it is stated that a layer is "on" another layer or substrate, the layer may be directly on another layer or substrate or a third layer may be disposed therebetween.

It will be understood that, although the terms first, second, third, etc., may be used herein to describe various elements, it should not be limited by these terms. These terms are only used to distinguish one element from another element.

As used herein, the singular forms "a," "an" and "the" are intended to include the plural forms as well, unless the context clearly indicates otherwise.

An identification code is used for the convenience of the description but is not intended to illustrate the order of each step. Each of the steps may be implemented in an order different from the illustrated order unless the context clearly indicates otherwise.

Hereinafter, the operation principles and embodiments of the disclosure will be described with reference to the accompanying drawings.

Figure 2:
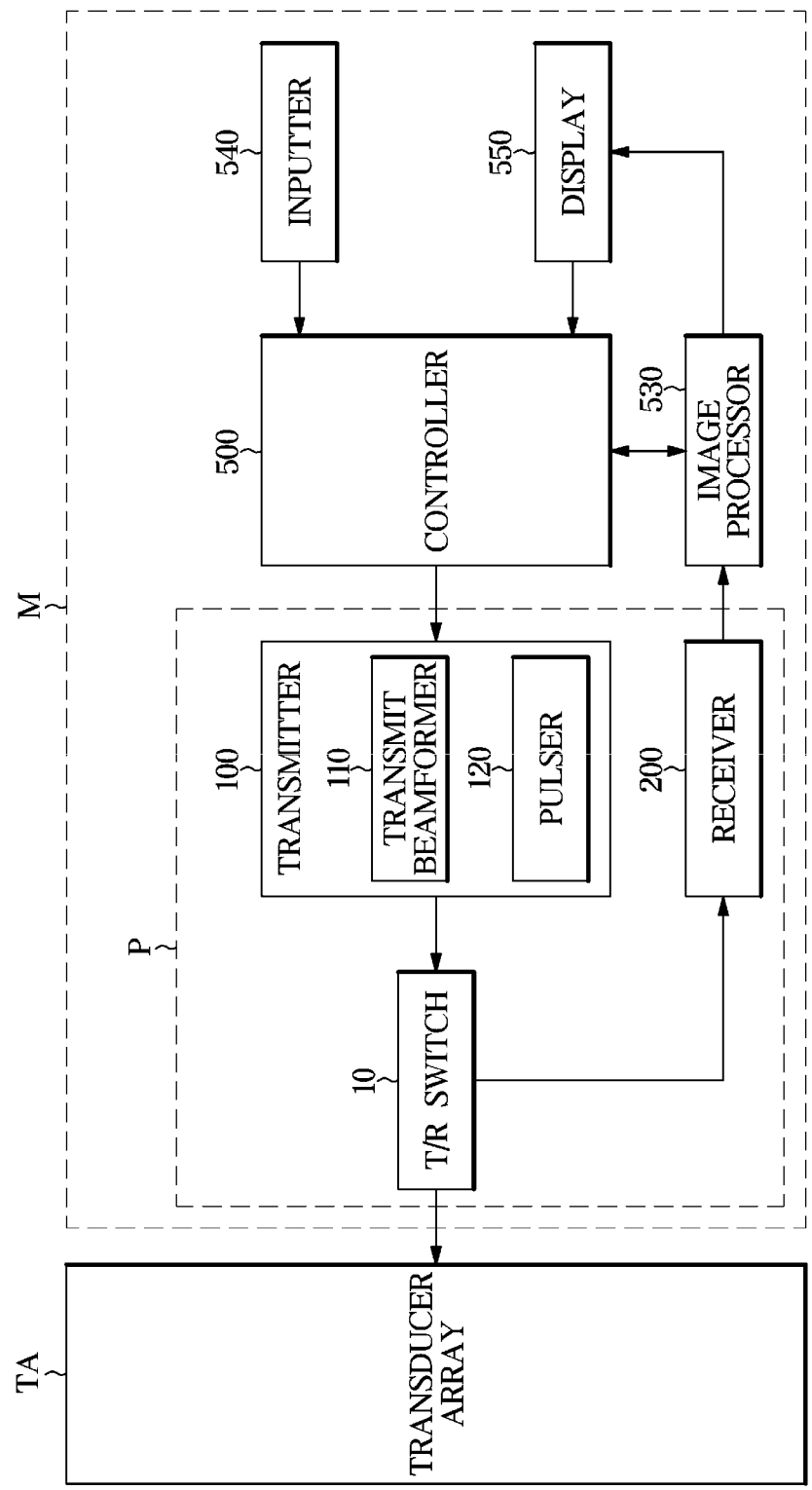
FIG. 2 is a control block diagram of an ultrasound imaging apparatus according to an embodiment of the disclosure.

FIG. 1 is a view illustrating an appearance of an ultrasound imaging apparatus according to exemplary embodiments of the disclosure, FIG. 2 is a control block diagram of an ultrasound imaging apparatus according to exemplary embodiments of the disclosure, and FIG. 3 is a control block diagram specifically illustrating a configuration of a main body of an ultrasound imaging apparatus according to exemplary embodiments of the disclosure.

Referring to FIG. 1, an ultrasound imaging apparatus 1 may include an ultrasound probe P configured to transmit ultrasound to an object, receive an ultrasound echo signal from the object, and convert the received ultrasound echo signal into an electrical signal; and a main body M connected to the ultrasound probe P and having an inputter 540 and a display 550 and configured to display an ultrasound image. The ultrasound probe P may be connected to the main body M of the ultrasound imaging apparatus 1 through a cable 5 to receive various signals required for controlling the ultrasound probe P, or transmit an analog signal or digital signal corresponding to the ultrasound echo signal received by the ultrasound probe P to the main body M. However, the embodiment of the ultrasound probe P is not limited thereto, and the ultrasound probe P may be implemented as a wireless probe to transmit and receive signals through a network formed between the ultrasound probe P and the main body M.

The cable 5 may be connected at one end to the ultrasound probe P and may be provided at the other end with a connector 6 that is coupled to or separated from in a slot 7 of the main body M. The main body M and the ultrasound probe P may exchange control commands or data using the cable 5. For example, when a user inputs information about a focal depth, a size or shape of an aperture, or a steering angle through the inputter 40, the information is transmitted to the ultrasound probe P through the cable 5 to thereby be used by a beamforming apparatus (not shown). Alternatively, when the ultrasound probe P is implemented as a wireless probe as described above, the ultrasound probe P is connected to the main body M through a wireless network, rather than the cable 5. Even when the main body M is connected to the main body M through a wireless network, the main body M and the ultrasound probe P may exchange the above-described control commands or data. As illustrated in FIG. 2, the main body M may include a controller 500, an image processor 530, an inputter 540, and a display 550.

The controller 500 may controls overall operations of the ultrasound imaging apparatus 1. In particular, the controller 500 may generate a control signal for controlling each component of the ultrasound imaging apparatus 1, for example, a transmitter 100, a T/R switch 10, a receiver 200, an image processor 530, the display 550, and the like illustrated in FIG. 2, and may control the operations of the above-described components. In the ultrasound imaging apparatus 1 illustrated in FIGS. 2 and 3, a transmission/reception beamformer is included in the ultrasound probe P rather than the main body M, but the transmission/reception beamformer may be included in the main body M instead of the ultrasound probe P.

The controller 500 may calculate delay profiles of a plurality of ultrasound transducer elements 60 constituting an ultrasound transducer array TA and calculate time delay values in accordance with distance differences between each of the plurality of ultrasound transducer elements 60 included in the ultrasound transducer array TA and a focal point of the object based on the calculated delay profiles. In addition, the controller 500 may control the transmission/reception beamformer in accordance therewith to generate transmission/reception signals.

The transducer array TA may be configured to be included in the main body M or the ultrasound probe P probe P.

Also, the controller 500 may control the ultrasound imaging apparatus 1 by generating control commands for the respective components of the ultrasound imaging apparatus 1 according to a user's instruction or command input through the inputter 540.

The image processor 530 may generate an ultrasound image of a target portion inside the object based on ultrasound signals focused by the receiver 200.

Referring to FIG. 3, the image processor 530 may include an image forming device 531, a signal processor 533, a scan converter 535, a storage 537, and a volume rendering device 539.

The image forming device 531 may generate a coherent two-dimensional (2D) image or three-dimensional (3D) image of the target portion inside the object based on the ultrasound signals focused by the receiver 20.

The signal processor 533 may convert information on the coherent image generated by the image forming device 531 into ultrasound image information according to a diagnosis mode, such as a brightness mode (B-mode) or a Doppler mode (D-mode). For example, when the diagnosis mode is set to the B-mode, the signal processor 533 may perform and analog/digital (A/D) conversion process, or the like and generate ultrasound image information for a B-mode image in real time. Alternatively, when the diagnosis mode is set to the D-mode, the signal processor 533 may extract information on phase changes from the ultrasound signal, calculate information on a blood stream corresponding to each point of cross-sectional image such as speed, power, and distribution, and generates ultrasound image information for a D-mode image in real time.

The scan converter 535 may convert the converted ultrasound image information received from the signal processor 533 and the converted ultrasound image information stored in the storage 537 into general video signals for the display 550 and transmit the converted signals to the volume rendering device 539.

The storage 537 may temporarily or non-temporarily store the ultrasound image information converted by the signal processor 533.

The volume rendering device 539 may perform volume rendering based on the video signals received from the scan converter 535, correct rendered image information to generate a final resultant image, and transmit the generated resultant image to the display 550.

The inputter 540 allows the user to input a command related to the operation of the ultrasound imaging apparatus 1. The user may input or set an ultrasound diagnosis start command, a diagnosis mode select command to select the B-mode, a motion mode (M-mode), the D-mode, an elastography mode (E-mode), or a 3D-mode, region of interest (ROI) setting information including size and position of a ROI, and the like through the inputter 540.

The B-mode image may refer to an image displaying the cross-section of the inside of the object and portions with strong echo signals are distinguished from portions with weak echo signals by modulating brightness. The B-mode image is generated based on information obtained from tens to hundreds of scan lines.

The M-mode may refer to an image representing changes over time in biometric information (e.g., brightness information) on a particular portion (M line) in a cross-sectional image (B-mode image). In general, the B-mode image and a M-mode image are simultaneously displayed on one screen to allow to the user to accurately diagnose by comparing and analyzing the two types of data.

The D-mode image may refer to an image of a moving object obtained by the Doppler effect in which a frequency of sound emitted from a moving object changes. Modes using the Doppler effect may further be classified into a power Doppler imaging (PDI) mode, a color flow (S Flow) mode, and a directional power Doppler imaging (DPDI) mode.

A PDI mode image may refer to an image representing the degree of Doppler signal or the number of structures (number of erythrocytes in blood). In the PDI mode, there is no aliasing signals due to less sensitivity to an angle of incidence and image attenuation caused by noise decreases. Also, since reflected Doppler energy is recorded, the PDI mode is very sensitive enabling detection of small blood vessels and blood streams with low speed.

The S Flow mode may provide a power image (PDI) representing the power of a Doppler signal in 2D distribution and a velocity image representing the velocity of the Doppler signal in 2D distribution. A S flow image may not only visualize blood streams in real time but also represent a wide range of blood stream statuses from a high velocity blood stream in a larger blood vessel to a low velocity blood stream in a smaller blood vessel.

A DPDI mode image may refer to a directional image representing information on a direction of a Doppler signal in 2D distribution in the PDI mode. Thus, the DPDI mode may detect information on blood streams more accurately than the PDI mode. In addition, the M-mode image may be generated in the D-mode.

The E-mode may refer to a method of obtaining an ultrasound elastography image by using elastography. In this regard, elastography refers to an analysis of a phenomenon in which elasticity of tissues decreases in a hard structure such as malignant mass, and thus the degree of deformation of the tissues by pressure decreases. An ultrasound elastography image refers to an image quantitatively representing stiffness of tissues. Particularly, the E-mode has been widely used in diagnosis of cervix cancer, breast cancer, or prostate cancer.

A 3D-mode image may refer to an image representing a geometric conformation or a space including X, Y, and Z values respectively representing depth, width, and height or a series of images indicating a stereoscopic feeling as a 3D shape or providing a stereoscopic effect. For example, the user may display a face shape of a fetus by using stereoscopic effects of the 3D-mode and provide parents of the fetus with the face shape.

Meanwhile, the operation of the disclosure may be performed in an ultrasound contrast agent (UCA) image obtained by entering an ultrasound contrast agent (UCA) image mode, but the disclosure is not limited to the corresponding mode, and the disclosure is not limited as long as the image of the object is derived based on the difference in the image signal.

The ultrasound imaging apparatus 1 may operate in the B-mode for obtaining a tissue image, a low voltage B-mode for obtaining a contrast agent image and the tissue image simultaneously, a contrast agent image mode for obtaining the contrast agent image, and the contrast agent image mode prior to administration of a contrast agent.

The contrast agent image described herein may be defined as a technique for imaging by using characteristics that the echo signal reflected from microbubbles constituting the ultrasound contrast agent (UCA) is displayed as a strong signal compared to a general tissue. A detailed description thereof will be described later.

The inputter 540 may include various devices allowing the user to input data, instructions, and commands, such as a keyboard, a mouse, a trackball, a tablet, or a touch screen module.

The display 550 may display a menu or information required for ultrasound diagnosis, an ultrasound image obtained during an ultrasound diagnosis process, and the like. The display 550 may display an ultrasound image of a target portion inside the object generated by the image processor 530. The ultrasound image displayed on the display 550 may be a B-mode ultrasound image, an E-mode ultrasound image, or a 3D ultrasound image. The display 550 may display various ultrasound images obtained according to the afore-mentioned modes.

The display 550 may be implemented using various known displays such as a cathode ray tube (CRT) and a liquid crystal display (LCD).

The ultrasound probe P may include the transducer array TA, the T/R switch 10, the transmitter 100, and the receiver 200 as illustrated in FIG. 2. The transducer array TA may be provided at one end of the ultrasound probe P. The ultrasound transducer array TA may refer to a one-dimensional (1D) or 2D array of a plurality of ultrasound transducer elements 60. While the ultrasound transducer array TA oscillates by pulse signals or alternating currents supplied thereto, ultrasound is generated. The generated ultrasound may be transmitted to the target portion inside the object. In this case, the ultrasound generated by the ultrasound transducer array TA may also be transmitted to a plurality of target portions inside the object. In other words, the generated ultrasound may be multi-focused and transmitted to the plurality of target portions.

The ultrasound generated by the ultrasound transducer array TA may be reflected by the target portion inside the object and then return to the ultrasound transducer array TA. The ultrasound transducer array TA may receive ultrasound echo signals returning after being reflected by the target portion. When an ultrasound echo signal arrives at the ultrasound transducer array TA, the ultrasound transducer array TA may oscillate at a predetermined frequency corresponding to a frequency of the ultrasound echo signal and output an alternating current having a frequency corresponding to the oscillation frequency. Thus, the ultrasound transducer array TA may convert the received ultrasound echo signal into an electric signal. Since each of the ultrasound transducer elements 60 may output an electric signal by receiving the ultrasound echo signal, the ultrasound transducer array TA may output electric signals of a plurality of channels.

The ultrasound transducer may be implemented using a magnetostrictive ultrasound transducer using a magnetostrictive effect of a magnetic material, a piezoelectric ultrasound transducer using a piezoelectric effect of a piezoelectric material, or a capacitive micromachined ultrasound transducer (cMUT) that receives ultrasound using oscillation of hundreds or thousands of micromachined thin films. In addition, any other types of transducers capable of generating ultrasound in accordance with electric signals or generating electric signals in accordance with ultrasound may also be used as the ultrasound transducer.

For example, the transducer elements 60 may include a piezoelectric vibrator or a thin film. When an alternating current is supplied from a power source, the piezoelectric vibrator or the thin film vibrates at a predetermined frequency in accordance with the supplied alternating current and generates ultrasound having the predetermined frequency in accordance with the vibration frequency. On the contrary, when an ultrasound echo signal having a predetermined frequency arrives at the piezoelectric vibrator or the thin film, the piezoelectric vibrator or the thin film vibrates in accordance with the ultrasound echo signal and outputs an alternating current of a frequency corresponding to the vibration frequency.

The transmitter 100 may apply transmit purses to the transducer array TA to control the transducer array TA to transmit ultrasound signals to the target portion inside the object. The transmitter 100 may include a transmit beamformer and a pulser. A transmit beamformer 110 may generate a transmit signal pattern in accordance with a control signal of the controller 500 of the main body M and outputs the transmit signal pattern to a pulser 120. The transmit beamformer 110 may generate the transmit signal pattern based on a time delay value of each of the ultrasound transducer elements 60 constituting the transducer array TA calculated by the controller 500 and transmit the generated transmit signal pattern to the pulser 120.

The receiver 200 may perform a predetermined processing on ultrasound echo signals received by the transducer array TA and performs receive beamforming. The receiver 200 may include a receive signal processor and a receive beamformer.

The receiver 200 may perform image processing and signal processing after receiving a signal from the transducer. The electric signals converted by the transducer array TA are input to the receive signal processor. The receive signal processor may amplify the electric signals converted from the ultrasound echo signals before processing the electric signals or performing time delay processing on the electric signals and may adjust gains or compensate attenuation according to depth. More particularly, the receive signal processor may include a low noise amplifier (LNA) to reduce noise of the electric signals received from the ultrasound transducer array TA and a variable gain amplifier (VGA) to control gain values in accordance with the input signals. The VGA may be, but is not limited to, a time gain compensator (TGC) to compensate gains in accordance with distance from the focal point.

The receive beamformer may perform beamforming for the electric signals received from the receive signal processor. The receive beamformer increases intensities of the signals received from the receive signal processor through superposition. The electric signals beamformed by the receive beamformer are converted into digital signals by an A/D converter and transmitted to the image processor 530 of the main body M. When the main body M includes the A/D converter, analog signals beamformed by the receive beamformer may also be transmitted to the main body M and converted into digital signals in the main body M.

Meanwhile, the main body may include at least one slot connected to a connector connected to the probe.

Alternatively, the receive beamformer may be a digital beamformer. The digital beamformer may include a storage to sample analog signals and store the sampled signals, a sampling period controller to control a sampling period, an amplifier to adjust a sample size, an anti-aliasing low pass filter to prevent aliasing before sampling, a bandpass filter to select a desired frequency band, an interpolation filter to increase a sampling rate while performing beamforming, a high-pass filter to remove a direct current (DC) component or a low frequency band signal, and the like.

Meanwhile, the controller may output a warning message to the display when the connector and the slot are connected and the current flowing from the acoustic probe is out of a predetermined reference range.

The controller can output a warning message to the display when the identification current identifying the ultrasound probe is out of a predetermined reference range.

Meanwhile, the identification current identifying the probe may mean a current identifying the ID of the probe.

Also, the controller can output a warning message to the display when the test current of the element of the ultrasound probe is out of a predetermined reference range.

The test current may mean a current for determining an error of an element of a transducer of a probe.

Meanwhile, the overcurrent protection circuit included in the main body may be used to determine that the above-described current is included in the predetermined range. Meanwhile, the controller can output a warning message to the display when the current flowing from the ultrasound probe to the overcurrent protection circuit is out of a predetermined reference range.

Meanwhile, the current flowing from the ultrasound probe used in the above-described operation can be used as a test signal for self-diagnosis of the ultrasound probe.

Specifically, the controller can output a warning message to the display when the test current of the element of the ultrasound probe is out of a predetermined reference range.

Meanwhile, if the current flowing from the ultrasound probe is included in the predetermined error range, the controller can determine that a failure has occurred in the connector.

In addition, in this case, the controller may output a warning message corresponding to a failure of the connector to the display.

Figure 3A:
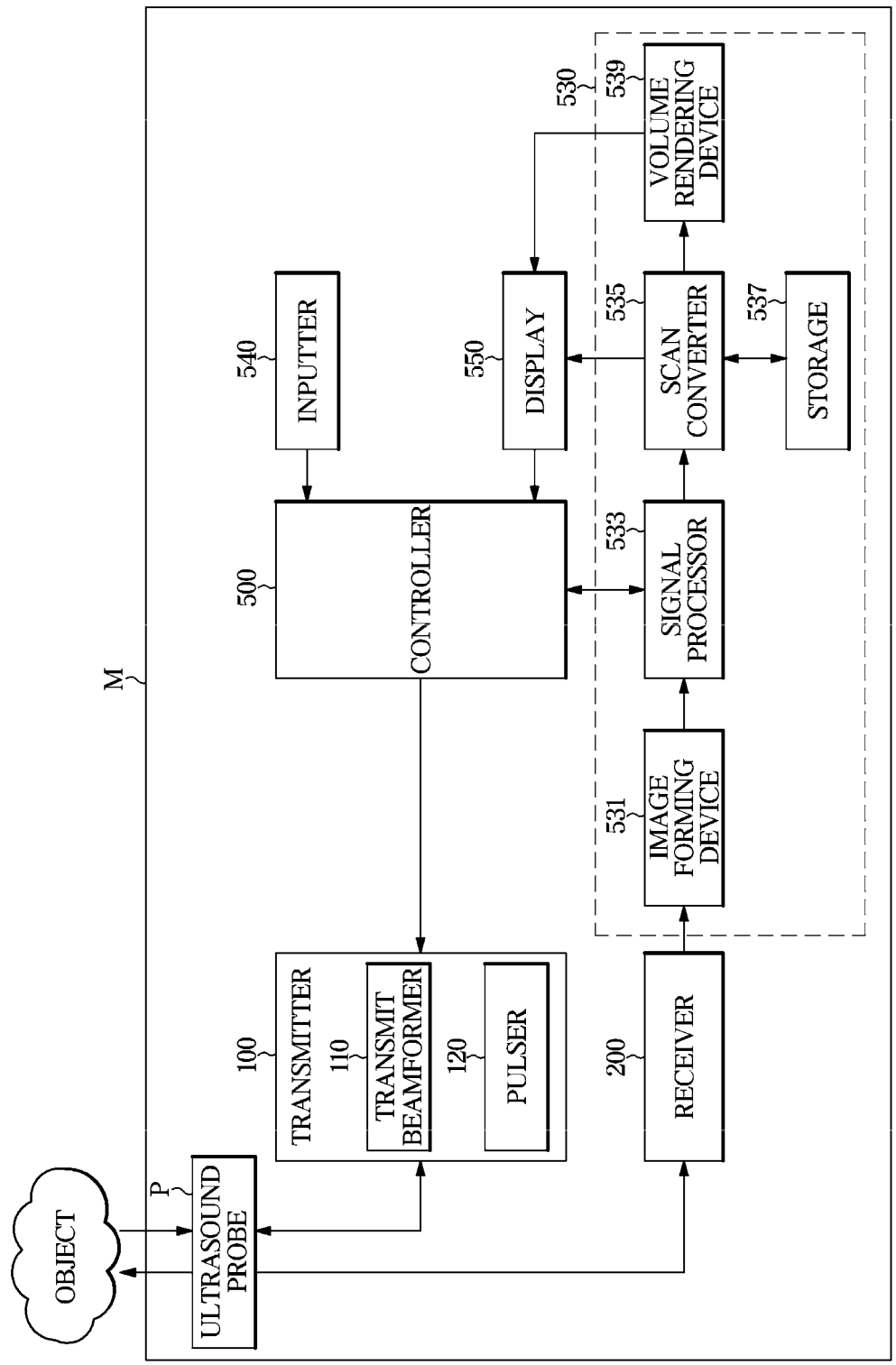
FIG. 3A is a control block diagram specifically illustrating a configuration of a main body of an ultrasound imaging apparatus according to an embodiment of the disclosure.
Figure 3B:
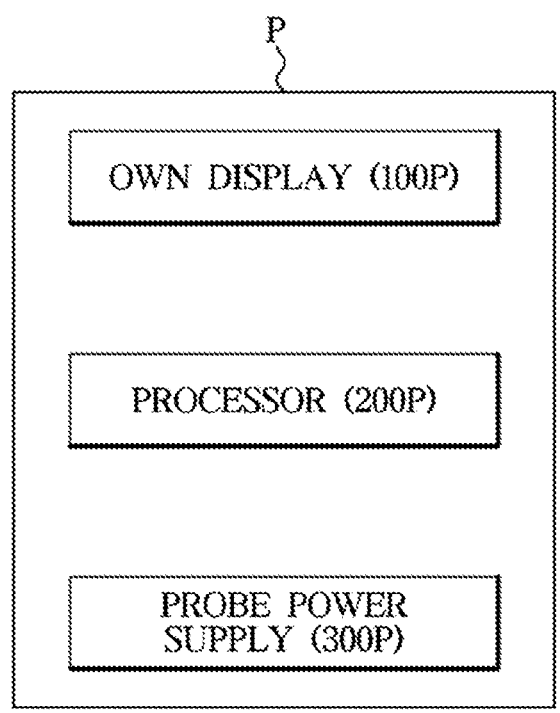
FIG. 3B is a control block diagram of an ultrasound probe according to an embodiment of the disclosure.

FIG. 3B is a control block diagram of an ultrasound probe according to an embodiment of the disclosure.

The above-described ultrasound probe may be provided as an insertion type probe.

The ultrasound probe itself includes an own display 100P, and the controller may output a warning message to the own display 100P.

Specifically, the probe may include a probe power supply 300P capable of applying a test current to the probe and an own display.

Meanwhile, the ultrasound probe may include at least one processor 200P that outputs a warning message to the own display when the test current generated based on the power supplied to the power supply exceeds a predetermined range.

Specifically, the ultrasound probe includes an own display, and the controller may output a warning message to the own display.

Meanwhile, the power supply included in the probe may be charged from power supplied by another device when the connector is connected to at least another device and the ultrasound probe transmits and receives an ultrasound signal.

Further, at least one processor 200P may control a power supply to supply current to the connector when a user inputs a self-diagnosis command.

The controller may be implemented using a memory (not shown) that stores data on algorithms to control the operation of components of the ultrasound imaging apparatus or programs to run the algorithms and a processor (not shown) that performs the aforementioned operation by using data stored in the memory. In this case, the memory and the processor may be implemented as separate chips. Alternatively, the memory and the processor may be implemented as a single chip.

At least one component may be added or deleted corresponding to performance of the components of the ultrasound imaging apparatus illustrated in FIGS. 3A and 3B. In addition, it will be readily understood by those skilled in the art that mutual positions of the components may be changed to correspond to performance or structure of a system.

Figure 4:
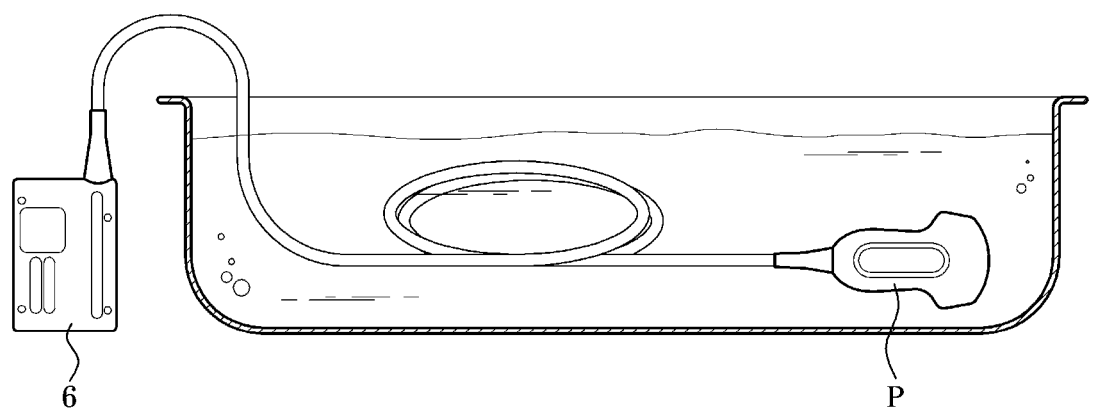
FIG. 4 is a view illustrating cleaning of an ultrasound probe according to an embodiment of the disclosure.

FIG. 4 is a view illustrating cleaning of an ultrasound probe according to an embodiment of the disclosure.

Referring to FIG. 4, disinfection/sterilization such as cleaning of a disinfectant is performed after probe use and diagnosis, and the probes may malfunction in the form of corrosion, precipitation, invasion, and deformation.

Meanwhile, although FIG. 4 shows an operation in which the probe P is provided in a disinfectant and disinfected, the connector 6 provided in the probe may also be disinfected together with the probe.

Meanwhile, the connector 6 may be provided as a switch box connected to the main body.

If the disinfectant remains, the connector 6 of the probe may fail due to the supply of current when connected to the main body.

The present disclosure can detect the residual of the disinfectant even when disinfection is performed in this manner. Hereinafter, this operation will be described in detail.

Figure 5:
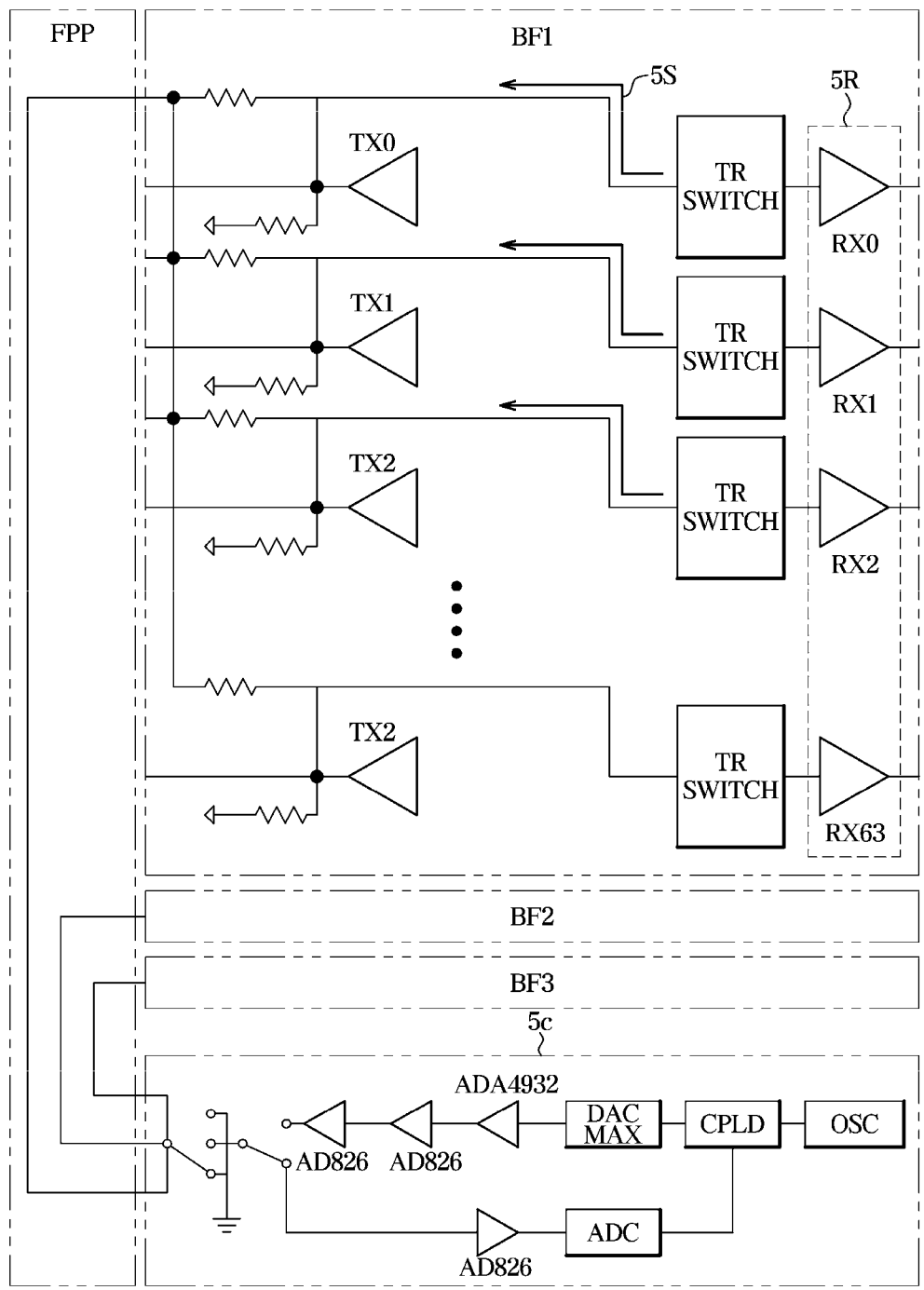
FIG. 5 is a schematic circuit diagram of an overcurrent protection circuit according to an embodiment of the disclosure.
Figure 6:
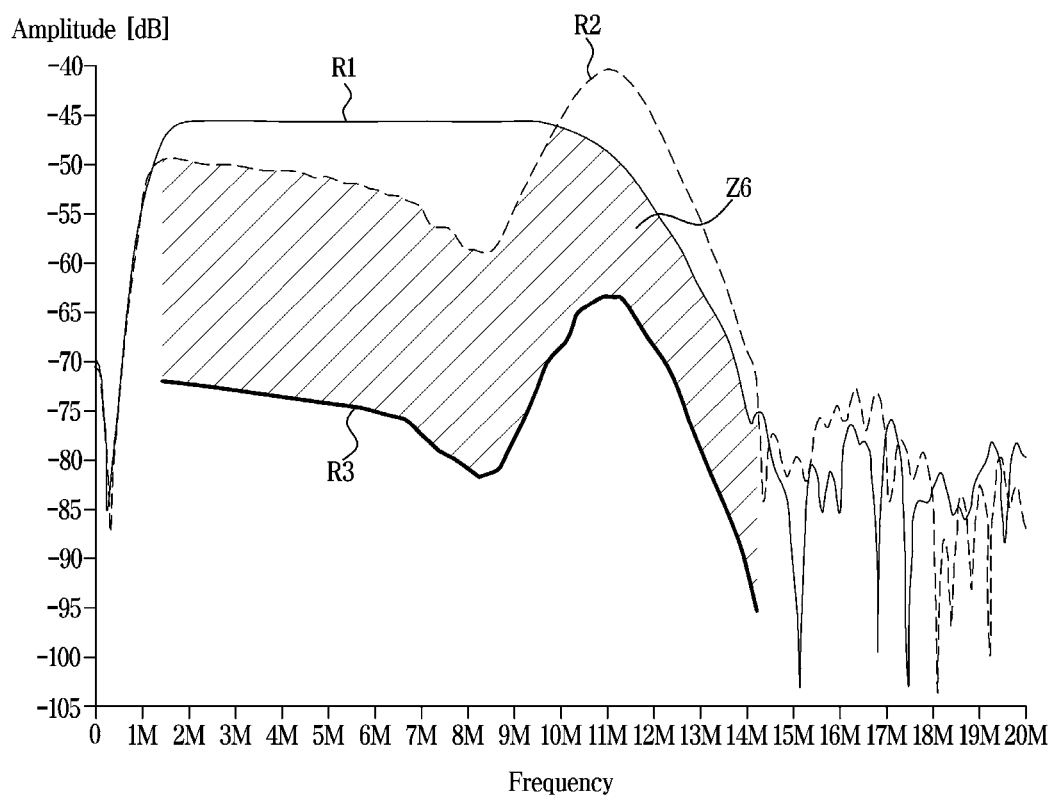
FIG. 6 is a graph illustrating a current flowing from an ultrasound probe and a predetermined reference range according to an embodiment of the disclosure.

FIG. 5 is a schematic circuit diagram of an overcurrent protection circuit according to an embodiment of the disclosure. FIG. 6 is a graph illustrating a current flowing from an ultrasound probe and a predetermined reference range according to an embodiment of the disclosure.

Referring to FIGS. 5 and 6, FIG. 5 shows a circuit used for self-diagnosis of a probe.

It shows the current 5S transmitted from the probe's receiving element 5R.

The current delivered from the probe can use the test signal of the receiving element 5R. Specifically, the current flowing from the ultrasound probe can be used as a test signal for self-diagnosis of the ultrasound probe.

Specifically, the ultrasound imaging apparatus may further include an overcurrent protection circuit 5C for testing the normal operation of the ultrasound probe.

The controller provided in the ultrasound imaging apparatus can output a warning message to the display when the current flowing from the ultrasound probe to the overcurrent protection circuit is out of a predetermined reference range.

On the other hand, the ultrasound imaging apparatus can compare the magnitude of the current that has acquired this operation.

Specifically, referring to FIG. 6, the controller may determine that the current flows through the ultrasound like R1 when the probe is not connected.

On the other hand, if the ultrasound operates normally, the current can flow in the same form as R2. That is, when a current flows like R1 or a current flows like R2, it can be determined that the probe operates normally.

That is, when current flows through the probes like R1 and R2, it can be determined that even the probe that has finished disinfection does not have residual disinfectant and operates normally.

Meanwhile, when the current received from the probe flows like R3, the controller of the imaging device may determine that the probe does not operate normally.

Meanwhile, when a current flows below R3 while driving the probe, the controller of the imaging apparatus may determine that the probe does not operate normally.

Therefore, if the driving current of the probe falls within the region of Z6, it can be determined that the probe operates normally.

Meanwhile, according to an embodiment, the controller may determine the region of Z6 as a predetermined reference range.

That is, the controller may determine a current flowing based on a normal probe, and may determine a current when the probe malfunctions in advance.

On the other hand, the controller can determine that the probe is operating normally if the current received from the probe is between normal flow and malfunctioning.

Normal operation of the probe may mean that there is little residual disinfectant in the probe.

Meanwhile, if the probe does not operate normally, it may mean that the amount of residual disinfectant in the probe is large. Therefore, in this case, the controller can display a warning message to the display.

Meanwhile, the operations described in FIGS. 5 and 6 are only one embodiment of the present disclosure, and the operation of determining a predetermined reference region is not limited thereto.

Figure 7:
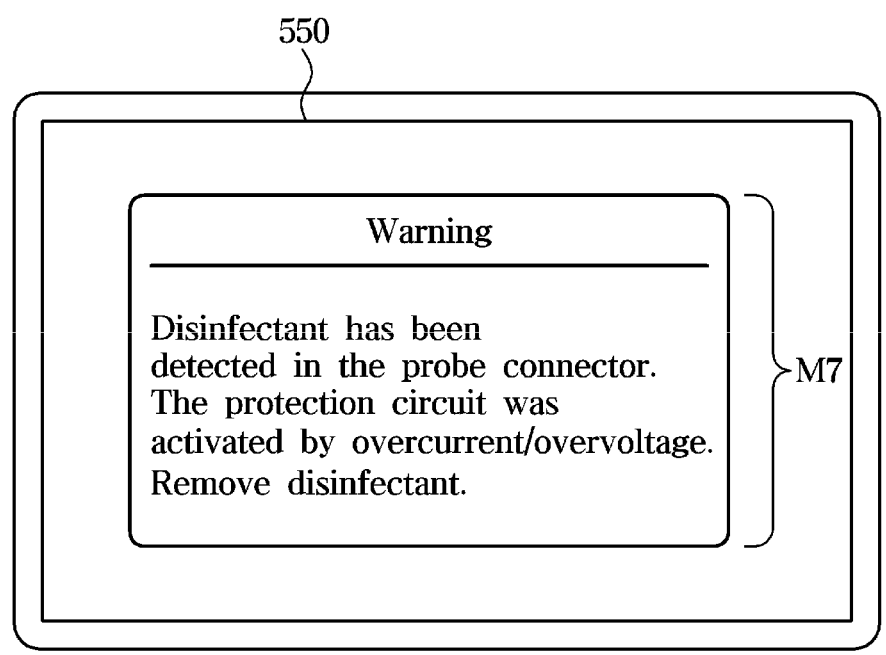
FIG. 7 is a view illustrating a warning message output on the display of the ultrasound imaging apparatus according to an embodiment of the disclosure.
Figure 8:
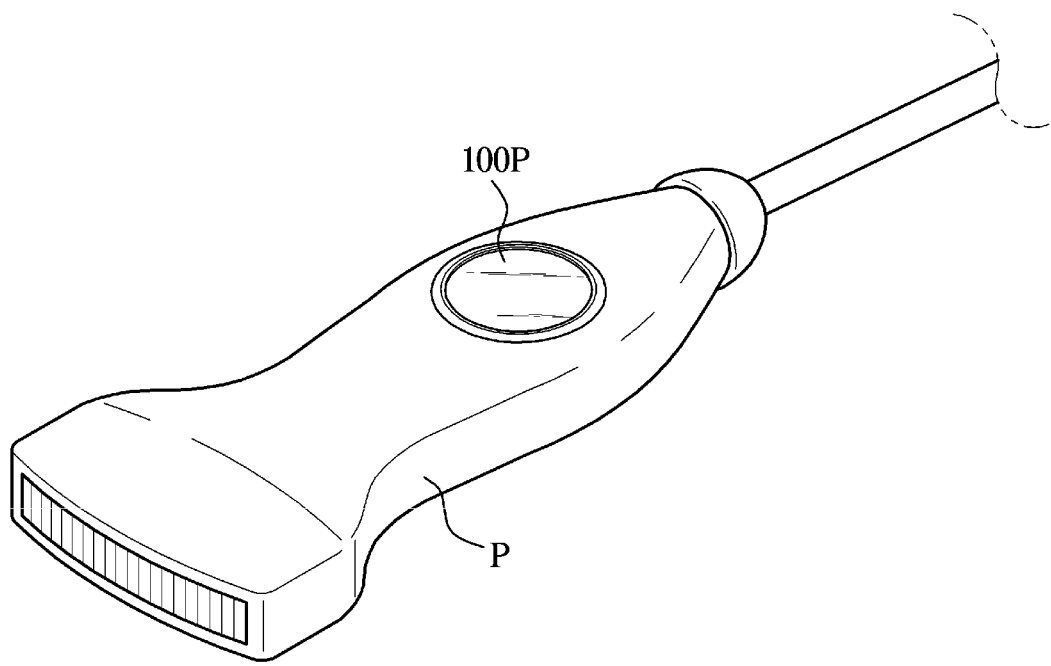
FIG. 8 is a view illustrating an own display included in the ultrasound probe according to an embodiment of the disclosure.

FIG. 7 is a view illustrating a warning message output on the display of the ultrasound imaging apparatus according to an embodiment of the disclosure. FIG. 8 is a view illustrating an own display included in the ultrasound probe according to an embodiment of the disclosure.

Referring to FIG. 7, the controller according to an embodiment may output a warning message M7 to the display when the current flowing from the ultrasound probe is out of a predetermined reference range.

Meanwhile, referring to FIG. 8, such a warning message may be output by the own display 100P provided in the probe itself.

Meanwhile, the probe may include a probe power supply capable of applying a test current to the probe and own display 100P.

Meanwhile, the ultrasound probe may include at least one processor that outputs a warning message to the own display 100P when a test current generated based on power supplied to the power supply exceeds a predetermined range.

Specifically, the ultrasound probe includes an own display 100P, and the controller may output a warning message to the own display.

Meanwhile, on the own display provided in the probe, a warning message may be output by a processor provided in the probe itself in addition to the controller provided in the main body.

Specifically, at least one processor provided in the ultrasound probe may control the probe power supply provided in the ultrasound probe to supply current to the connector when a user inputs a self-diagnosis command.

The processor provided in the ultrasound probe can determine whether or not the disinfectant remains in the ultrasound probe based on this.

Meanwhile, according to an embodiment, the controller may display "X" on its own display when disinfectant remains in the probe.

In addition, according to another embodiment, the controller may display "?" on its own display when the disinfectant remains in the probe and inspection is required.

In this way, the probe can determine whether the disinfectant remains in the probe itself without connecting the connector to the main body.

Meanwhile, the output format of the warning message illustrated in FIGS. 7 and 8 is only an embodiment of the present disclosure, and the format of the message is not limited thereto.

Figure 9:
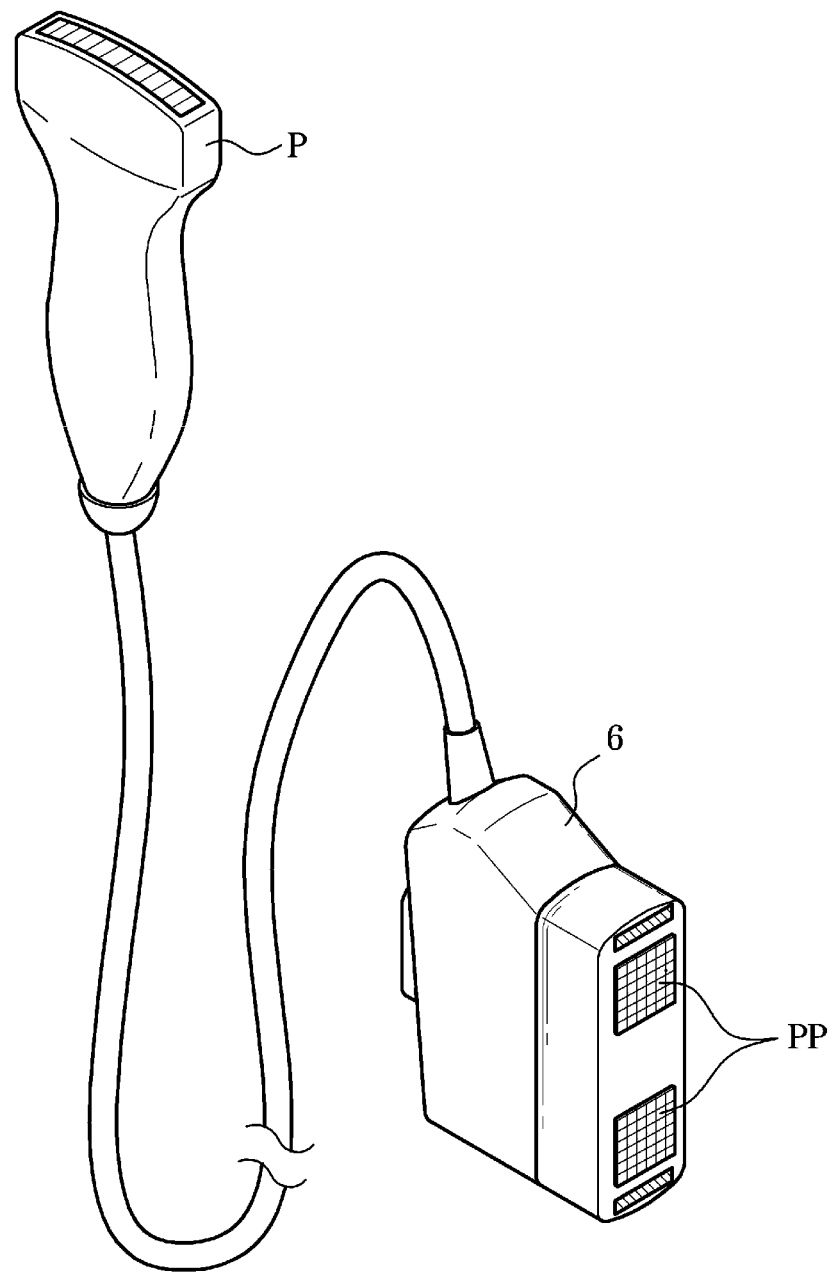
FIG. 9 is a view for illustrating the operation related to the connector of the ultrasound probe according to an embodiment of the disclosure.

FIG. 9 is a view for illustrating the operation related to the connector of the ultrasound probe according to an embodiment of the disclosure.

The controller according to an embodiment of the present disclosure may determine that a failure has occurred in the connector when the current flowing from the ultrasound probe P is included in the predetermined error range.

Specifically, the ultrasound probe may be provided with a connector 6 connected to the main body, and the connector may include a pin PP connected to the main body. Meanwhile, if the connector pin (PP) is bent or damaged, the current flowing through the probe may be included in the error range.

Meanwhile, the predetermined error range may be determined as a range numerically corresponding to the reference range described above, but may be defined as a range of a current for detecting an error of the probe connector 6.

Meanwhile, as described above, if the current received from the probe falls within the error range, the controller may output a warning message corresponding to a failure of the connector to the display.

Figure 10:
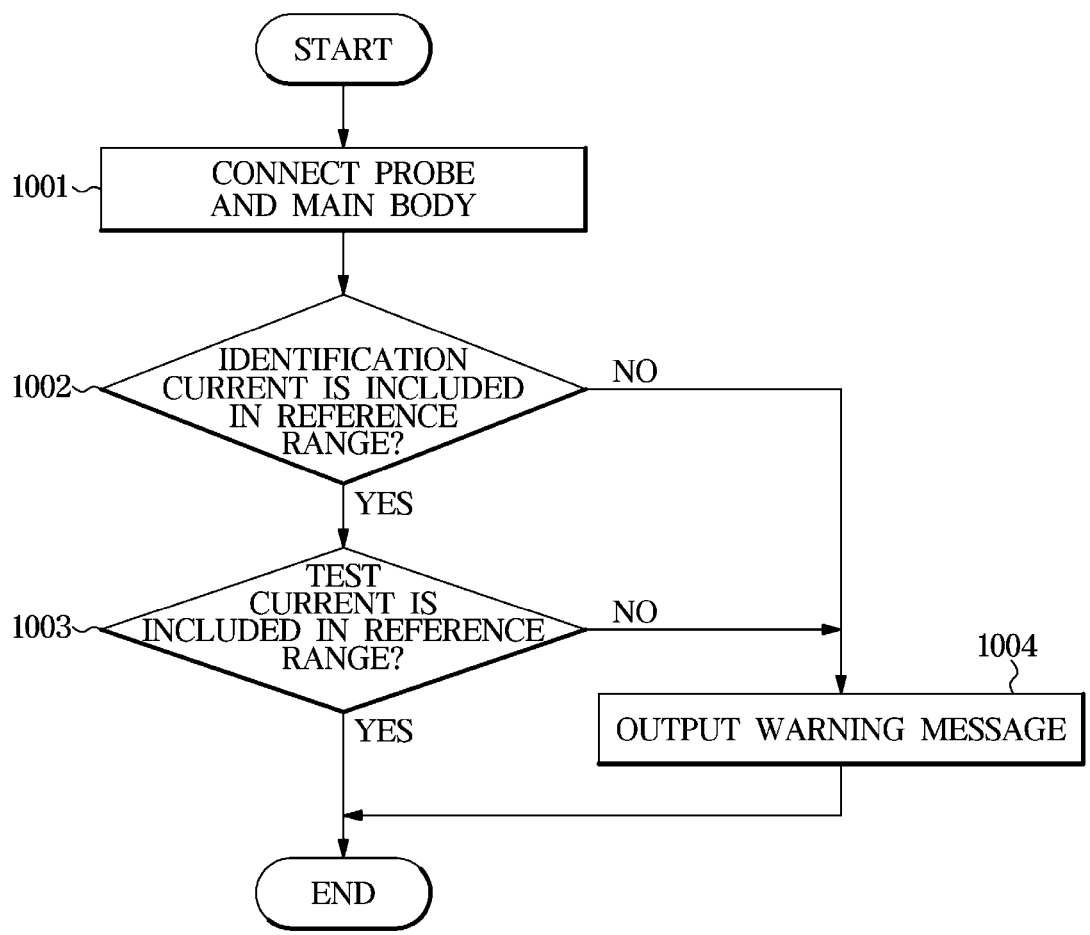
FIG. 10 is a flow chart according to an embodiment of the disclosure.

FIG. 10 is a flow chart according to an embodiment of the disclosure.

Referring to FIG. 10, the probe and the main body may be connected by respective connectors and slots (1001). Meanwhile, if the identification current identifying the probe is not included in the reference range, the ultrasound imaging apparatus may output a warning message to the display (1004).

On the other hand, if the identification current flowing from the ultrasound is included in the reference range, but the test current for examining the ultrasound probe is not included in the reference range, the controller can output a warning message through the display (1004).

Meanwhile, the disclosed exemplary embodiments may be implemented in the form of a recording medium storing instructions that are executable by a computer. The instructions may be stored in the form of a program code, and when executed by a processor, the instructions may generate a program module to perform operations of the disclosed exemplary embodiments. The recording medium may be implemented non-transitory as a computer-readable recording medium.

The non-transitory computer-readable recording medium may include all kinds of recording media storing commands that can be interpreted by a computer. For example, the non-transitory computer-readable recording medium may be, for example, ROM, RAM, a magnetic tape, a magnetic disc, flash memory, an optical data storage device, etc.

Embodiments of the disclosure have thus far been described with reference to the accompanying drawings. It will be obvious to those of ordinary skill in the art that the disclosure may be practiced in other forms than the embodiments as described above without changing the technical idea or essential features of the disclosure. The above embodiments are only by way of example, and should not be interpreted in a limited sense.

An ultrasound probe, an ultrasound imaging apparatus, and a control method thereof according to an embodiment can efficiently and quickly determine whether a disinfectant remains in the ultrasound probe or whether the ultrasound is operating normally, without changing the structure of the ultrasound imaging device.

What is claimed is:

1. An ultrasound imaging apparatus comprising:
an ultrasound probe comprising a connector;
a main body including at least one slot connected to the connector;
a display provided on the main body; and
a controller configured to output a first warning message or a second warning message to the display based on a current flowing from the ultrasound probe when the connector and the at least one slot are connected, and
wherein the controller is composed of at least one processor comprised in the main body and is configured to:
in response to determining that the connector is connected to the at least one slot, receive an identification current corresponding to an identifier (ID) of the ultrasound probe from the ultrasound probe and determine whether the identification current is out of a predetermined reference range,
in response to determining that the identification current is out of the predetermined reference range, output the first warning message for notifying a remaining of a disinfectant to the display,
in response to determining that the identification current is included in the predetermined reference range, receive a test current for determining an error of an element of a transducer of the ultrasound probe from the ultrasound probe, determine whether the test current is out of the predetermined reference range and determine whether the test current is in a predetermined error range,
in response to determining that the test current is out of the predetermined reference range, output the first warning message to the display,
in response to determining that the test current is in the predetermined error range, output the second warning message for notifying a failure of the connector to the display, and
in response to determining that the test current is included in the predetermined reference range and out of the predetermined error range, determine that the ultrasound probe operates normally.

2. The ultrasound imaging apparatus according to claim 1, wherein the main body comprises an overcurrent protection circuit, and
the controller is configured to output the first warning message to the display when the identification current or the test current flowing from the ultrasound probe to the overcurrent protection circuit is out of the predetermined reference range.

3. The ultrasound imaging apparatus according to claim 1, wherein the test current flowing from the ultrasound probe comprises a current used as a test signal for self-diagnosis of the ultrasound probe.

4. The ultrasound imaging apparatus according to claim 1, wherein the ultrasound probe is an insertion type probe which is able to be inserted into an object.

5. The ultrasound imaging apparatus according to claim 1, wherein the ultrasound probe comprises a display, and
the controller is configured to output the first warning message or the second warning message to the display of the ultrasound probe.

6. A control method of an ultrasound imaging apparatus comprising an ultrasound probe comprising a connector, a main body comprising at least one slot connectable to the connector, a display provided on the main body, the method comprising:
in response to determining that the connector is connected to the at least one slot, receiving an identification current corresponding to an identifier (ID) of the ultrasound probe from the ultrasound probe and determining whether the identification current is out of a predetermined reference range;
in response to determining that the identification current is out of the predetermined reference range, outputting a first warning message for notifying a remaining of a disinfectant to the display,
in response to determining that the identification current is included in the predetermined reference range, receiving a test current for determining an error of an element of a transducer of the ultrasound probe from the ultrasound probe, determining whether the test current is out of the predetermined reference range and determining whether the test current is in a predetermined error range,
in response to determining that the test current is out of the predetermined reference range, outputting the first warning message to the display,
in response to determining that the test current is in the predetermined error range, outputting a second warning message for notifying a failure of the connector to the display, and
in response to determining that the test current is included in the predetermined reference range and out of the predetermined error range, determining that the ultrasound probe operates normally.

7. The control method according to claim 6, wherein the main body comprises an overcurrent protection circuit, and
wherein the outputting the first warning message comprises:
outputting the first warning message to the display when the identification current or the test current flowing from the ultrasound probe to the overcurrent protection circuit is out of the predetermined reference range.

8. The control method according to claim 6, wherein the test current flowing from the ultrasound probe comprises a current used as a test signal for self-diagnosis of the ultrasound probe.

9. The control method according to claim 6, wherein the ultrasound probe is an insertion type probe which is able to be inserted into an object.

10. The control method according to claim 6, wherein the ultrasound probe comprises a display, and
   wherein the outputting the first warning message or the second warning message comprises:
   outputting the first warning message or the second warning message to the display of the ultrasound probe.

* * * * *